July 15, 1975 J. C. MIKKELSEN Plant Pat 3,744
POINSETTIA PLANT
Filed April 29, 1974
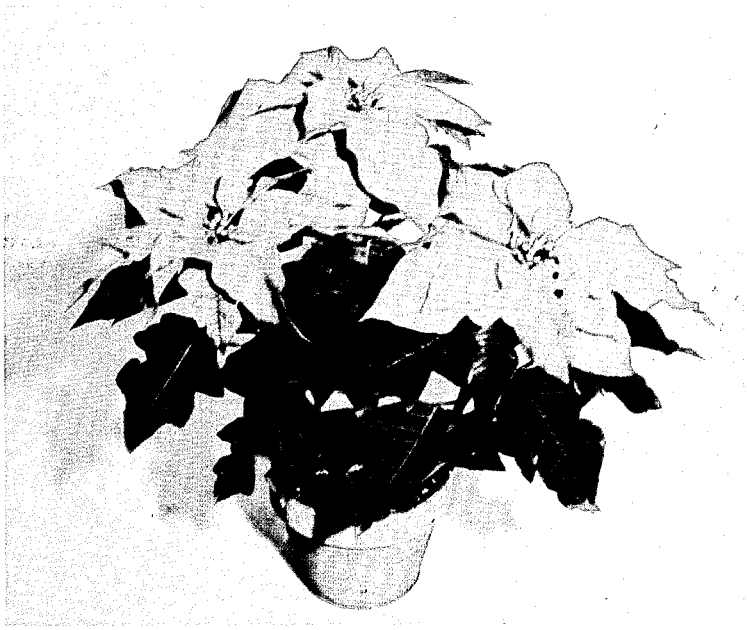

United States Patent

Plant Pat. 3,744

Patented July 15, 1975

3,744

POINSETTIA PLANT

James C. Mikkelsen, Ashtabula, Ohio, assignor to Mikkelsens Inc., Ashtabula, Ohio

Filed Apr. 29, 1974, Ser. No. 465,242

Int. Cl. A01h *5/03*

U.S. Cl. Plt.—86 1 Claim

The present invention relates to a new and distinctive cultivar of poinsettia plant known by the varietal name Mikkel Cardinal II, and botanically known as *Euphorbia pulcherrima.*

The new cultivar is a seedling resulting from controlled hybridizing of two distinct poinsettia varieties under my control and supervision, with the parent varieties being unpatented and identified for breeding purposes by breeding numbers 66–248–1 and 69–1027–8.

The new cultivar has been asexually reproduced by cuttings in the greenhouses of Mikkelsens Inc., Ashtabula, Ohio, and has been found to retain its distinctive characteristics through successive propagations under various environments.

The following characteristics distinguish the new cultivar from its parents and from other poinsettias commercially known and used in the floriculture industry:

(1) Very fast flowering, will flower in 45–48 days with an 11½ hour daylength, when grown at 18°–19° C.; if grown at 16°–17° C., with resultant lower fuel costs, it will flower in 56–60 days.

(2) Maintains bright red bracts under adverse conditions of high light and high temperature, a most valuable quality for the home and southern poinsettia production areas.

(3) The number of individual cyathias in the inflorescence is considerably less than in most present cultivars, being as few as 4 or 5 to 8 or 10.

(4) Bract surfaces are not smooth but rippled as in the unpatented variety Stoplight, developed by the U.S. Dept. of Agriculture.

(5) Growth of the stem is quite upright, with the stems being strong and rigid.

(6) When the terminal apex is removed during vegetative growth, branching occurs in three to five or more of the top leaf axis. Branched plants have a formal appearance.

(7) Leaves are distinctive with deep and well rounded sinuses. Leaf pattern is distinctively oakleaf.

(8) Good to excellent keeping qualities but less than the cultivar Paul Mikkelsen, disclosed in U.S. Plant Pat. No. 2,328.

The accompanying colored photographic drawing illustrates the overall appearance of the new cultivar, with the colors being as true as possible to obtain in color reproductions of this type.

The following is a detailed description of the new cultivar based on plants produced under commercial practices in the greenhouses of Mikkelsens Inc., Ashtabula, Ohio. It will be understood that growth rate, response period, bract color, etc. may vary significantly with varying environmental conditions such as temperature, daylength, and light intensity. The description also reflects trialling of the new cultivar at West Palm Beach, Fla.

Color references in the following description are to the Royal Horticultural Society Colour Chart except where general color terms of ordinary dictionary significance are used.

*Parentage*: Seedling from controlled crossing of poinsettia #66–248–1 with poinsettia #69–1027–8.

*Form of Plant*: Upright, non-self branching, strong stems with thick walls. During the normal fall growing season stem diameter will measure 7–10 mm.

*Growth Habit*: Quite rapid, during 12–14 hour daylength period at 22°–28° C.; healthy plants will grow four to six cm. per week. Inefficient grower during dark winter months.

*Rooting*: Excellent, in 15–20 days provided rooting media temperature is 22° C. and daylength 12–14 hours. Roots are coarse and abundant.

*Blooming Habit*: Flowering is very responsive in a 11½ to 12 hour daylength and 18° C. night temperature in 45 days.

*Blooming Season*: Natural season in Ohio and Florida is as early as Nov. 10–15. Cultivar is readily forced with proper 11½ hour daylength and temperatures between 16° C. and 26° C. anytime of year.

*Foliage*:

- *Size*: Short petiole, blade measuring 6–8 cm. wide and 10–14 cm. long.
- *Quantity*: Average.
- *Color*: New foliage—upper side—Green between 146A–137C; under side—Green 146–C. Old foliage—upper side—Green between 135A–139A; under side—Green between 137C–D.
- *Shape*: Oakleaf.
- *Texture*: Upper side—smooth glabrous. Underside—veins protrude, dull appearance.
- *Edge or margin*: Deep, long rounded sinuses.
- *Aspect*: Nearly horizontal; heavy, strong petioles.
- *Disease resistance*: No apparent susceptability to mildew or botrytis. When compared to present day cultivars, the new cultivar seems quite tolerable to air pollution; is very tolerable to extraneous light pollution.

*Flowers* (cyathia):

- *Borne*: In very compact inflorescence—clustered. Individual cyathia pedicels rarely elongate.
- *Quantity*: Less than for either parent or other cultivars. Often as few as four to upwards of ten in the initial flowering.
- *Continuity*: The cyathias absciss under normal environments of the home in four to six weeks. Immature syathias—green 146C–D. Mature cyathias 5 mm. in diameter, 15 mm. long, green near 145–A.

*Bracts*: Are four to six cm. wide and ten to twelve cm. long ending in a sharp, slightly twisted point. Edges are slightly wavy in the areas of the sinuses. Top sursurface is ruffled or puckered resembling seersucker. Petioles are short giving a tight appearance to the involucre.

- *Color*: Top—between red 45A and bright red 46A. Under—red 50A.

*Reproductive Organs:*

- *Stamens*: Color, red 46–D, anthers red.
- *Pollen*: Color, Yellow 13–D.
- *Styles*: Color, red 46–A.
- *Ovaries*: Color, green 143–C.
- *Nectar cups*: Normally single, width equals diameter of the cyathia, top surface orange/red, lower area yellow/orange 23–B, narrow red band near base of cup.

In cross pollinating, this cultivar to date has been a poor seed producer.

I claim:

1. A new and distinct poinsettia plant characterized particularly by its very fast flowering, in 45–48 days with an 11½ hour daylength when grown at 18°–19° C.; its excellent color retention under high light and high temperature conditions; decreased number of cyathias in the inflorescense; rippled bract surfaces; strong and rigid stems; excellent branching when the terminal apex is removed, giving the plant a formal appearance; good to excellent keeping qualities, and by its distinctive leaves, which have an oakleaf pattern with deep and well rounded sinuses.

No references cited.

ROBERT E. BAGWILL, Examiner